United States Patent [19]

Lee et al.

[11] Patent Number: 4,822,905

[45] Date of Patent: Apr. 18, 1989

[54] CERTAIN 2-(2-(SUBSTITUTED PHENYL)ACETYL)-1,3-CYCLOHEXANEDIONES

[75] Inventors: David L. Lee, Martinez; Donald R. James, El Sobrante; William J. Michaely, Richmond, all of Calif.

[73] Assignee: Stauffer Chemical Company, Westport, Conn.

[21] Appl. No.: 872,070

[22] Filed: Jun. 9, 1986

[51] Int. Cl.$^4$ ............................................. C07C 49/657
[52] U.S. Cl. ..................................... 558/414; 568/31; 568/42; 568/329; 549/446; 549/362; 71/88; 71/98; 71/103; 71/105; 71/123
[58] Field of Search ..................... 568/329, 31, 42; 71/123, 106; 558/414

[56] References Cited

U.S. PATENT DOCUMENTS

| | | | |
|---|---|---|---|
| 4,350,705 | 9/1982 | Hamano et al. | 568/329 |
| 4,517,013 | 5/1985 | Becher et al. | 71/106 |
| 4,560,403 | 12/1985 | Motojima et al. | 71/106 |

FOREIGN PATENT DOCUMENTS 0090262 10/1983 European Pat. Off. .
0162336 11/1985 European Pat. Off. .

OTHER PUBLICATIONS

Soviet Inventions III "Biologically active acyl etc" Section CH Week C 04 3/5/80.

Motojima et al "Cyclohexane Derivatives Having etc" CA 102:131584r (1985).
Ihara Chem "Plant Growth Regulating Cyclohexanes" GA 100:85308n (1984).
Akhrem et al "3,4-dihydro-10-hydroxy-1(2H)-etc" GA 103:123198y (1985).

Primary Examiner—Glennon H. Hollrah
Assistant Examiner—A. A. Owens
Attorney, Agent, or Firm—Edwin H. Baker

[57] ABSTRACT

Compounds having the structural formula

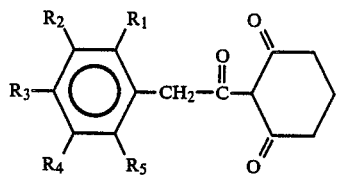

wherein $R_1$, $R_2$, $R_3$, $R_4$ and $R_5$ are the same or different and are selected from the group consisting of hydrogen, chlorine, bromine, iodine, nitro, alkyl having from 1 to 4 carbon atoms, alkoxy having from 1 to 4 carbon atoms, trifluoromethyl, trifluoromethoxy, cyano, alkylsulfonyl, and alkylthio having from 1 to 4 carbon atoms, and wherein $R_2$ and $R_3$ or $R_3$ and $R_4$ together can be methylene or ethylenedioxy.

4 Claims, No Drawings

CERTAIN 2-(2-(SUBSTITUTED PHENYL)ACETYL)-1,3-CYCLOHEXANEDIONES

BACKGROUND OF THE INVENTION

This invention relates to certain 2-[2-(substituted phenyl)acetyl]-1,3-cyclohexanediones, compounds which have been found to be effective herbicides and plant growth regulators.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and post-emergence herbicides. The pre-emergence herbicides are normally incorporated into the soil prior to the emergence of the weed plants from the soil, and the post-emergence herbicides are normally applied to plant surfaces after emergence of the weeds or other unwanted plants from the soil.

THE PRIOR ART

Compounds having the structural formula

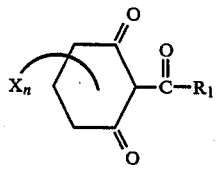

wherein X can be an alkyl, n can be 0, 1, or 2, and $R_1$ can be phenyl or substituted phenyl are described in Japanese Patent Application No. 84632-1974 as being intermediates for the preparation of herbicidal compounds of the formula

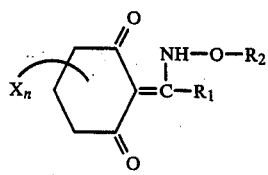

wherein $R_1$, X and n are as defined above and $R_2$ is alkyl, alkenyl, or alkynyl. Specifically taught herbicidal compounds of this latter group are those where n is 2, X is 5,5-dimethyl, $R_2$ is allyl and $R_1$ is phenyl, 4-chlorophenyl or 4-methoxyphenyl.

The precursor intermediates for these three specifically taught compounds have no or almost no herbicidal activity.

U.S. patent application Ser. No. 361,658, filed Mar. 25, 1982, discloses certain 2-(2-substituted benzoyl)-1,3-cyclohexanediones to be effective herbicides. The compounds of this invention are similar to but different from the disclosed benzoyl cyclohexane diones, and have exceptional herbicidal activity.

The term "alkyl" is used herein in its normal meaning and is intended to include both straight-chain and branched-chain groups.

The term "herbicide", as used herein, means a compound or composition which controls or modifies the growth of plants. By the term "herbicidally effective amount" is meant any amount of such compound or composition which causes a modifying effect upon the growth of plants. By "plants" is meant germinant seeds, emerging seedlings and established vegetation, including roots and above-ground portions. Such controlling or modifying effects include all deviations from natural development, such as killing, retardation, defoliation, regulation, stunting, tillering, leaf burn, dwarfing and the like.

DESCRIPTION OF THE INVENTION

This invention relates to certain novel 2-[(2-(substituted phenyl)acetyl)]-1,3-cyclohexanediones as herbicides. The compounds of this invention have the following structural formula

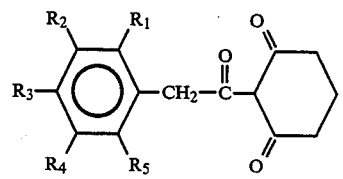

wherein $R_1$, $R_2$, $R_3$, $R_4$ and $R_5$ are the same or different and are selected from the group consisting of hydrogen, chlorine, bromine, iodine, nitro, alkyl having from 1 to 4 carbon atoms, alkoxy having from 1 to 4 carbon atoms, trifluoromethyl, trifluoromethoxy, cyano, alkylsulfonyl, and alkylthio having from 1 to 4 carbon atoms, and wherein $R_2$ and $R_3$ or $R_3$ and $R_4$ together can be methylene or ethylenedioxy.

These compounds can also exist in tautomeric form, and this invention encompasses the tautaumeric forms of cyclohexanediones described herein.

The compounds of this invention are active herbicides of a general type. That is, they are herbicidally effective against a wide range of plant species. The method of controlling undesirable vegetation of the present invention comprises applying an herbicidally effective amount of the above-described compounds to the area where control is desired.

The compounds of the present invention can be prepared by the following general method.

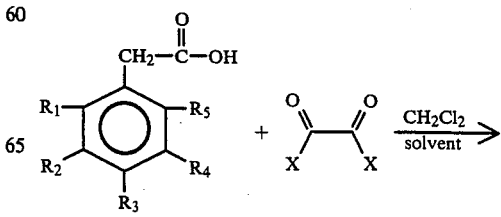

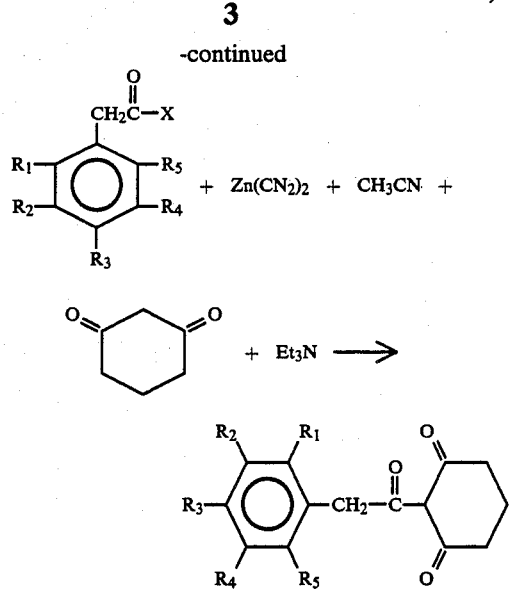

where X is a halogen and $R_1$-$R_5$ are as previously defined herein.

Generally, equimolar amounts of the dione and substituted phenylacetyl chloride are used, along with a slight mole excess of zinc cyanide. The two reactants and the zinc cyanide are combined in a solvent such as acetonitrile. A slight mole excess of triethylamine is slowly added to the reaction mixture with cooling. The mixture is stirred at reflux for 1 hour.

The reaction product is worked up by conventional techniques.

The following Examples teach the synthesis of representative compounds of this invention.

EXAMPLE I

2-[2-(2-Chlorophenyl)acetyl]-1,3-cyclohexanedione

To a solution of 17.1 grams (g) (0.1 mole) of (2-chlorophenyl) acetic acid in 100 milliliters (ml) of dichloromethane and 0.5 ml of dimethylformamide was added 19.0 g (0.15 mole) of oxalyl chloride dropwise over a 30 minute period. Evolution of gas commenced and lasted for approximately 30 minutes, after which the excess liquids were removed in vacuo. To the residue was added 100 milliliters (ml) of acetonitrile and 12.0 g (0.1 mole) of zinc cyanide, and the mixture was stirred for 15 minutes at room temperature. Thereafter, 11.2 g (0.1 mole) of 1,3-cyclohexanedione was added, followed by the dropwise addition of 15.0 g (0.148 mole) of triethylamine over a five minute period. The exothermic reaction reached approximately 50° C., after which it subsided. The mixture was heated at reflux for approximately one hour, then cooled to room temperature and the acetonitrile was removed in vacuo. To the residue was added 2N hydrogen chloride (to decompose the zinc salts), and ethyl ether. The various layers were separated, and the organic layer was washed with 5% potassium carbonate. The aqueous layer was acidified and extracted with dichloromethane three times. The dichloromethane layer was dried over magnesium sulfate, and the excess dichloromethane was roto-evaporated off. The crude product that was obtained was then stirred with a 5% Cu(OAc)$_2$ solution. The blue copper complex that resulted was filtered, and then decomposed with 6N HCl. The acidic solution was extracted with dichloromethane. After drying over MgSO$_4$, the dichloromethane was removed in vacuo to afford 1.2 g of a brown semi-solid which was identified as the subject compound.

EXAMPLE II 2-(4-trifluoromethylphenylacetyl)-1,3-cyclohexanedione

To a solution of 10 g of trifluoromethylphenylacetic acid (0.049 mole) dissolved in 100 ml dichloromethane and 0.5 ml dimethylformamide was added 8.9 g (0.07 mole) of oxalyl chloride dropwise over ½ hour. After the evolution of gases had ceased, the liquid was roto-evaporated. To the residue was added 5.75 g (0.049 mole) of zinc cyanide and approximately 100 ml of acetonitrile. The mixture was stirred for 15 minutes at room temperature, and then 5.5 g (0.49 mole) of 1,3-cyclohexanedione was added, followed by dropwise addition of 6.06 g (0.06 mole) of triethylamine. After the exothermic reaction had subsided, the mixture was then refluxed for one hour. Thereafter it was cooled to room temperature and the acetonitrile was removed in vacuo. To the residue was added 2N hydrochloric acid, and the mixture was extracted with ether, after which the organic layer was washed with 5% potassium carbonate. The aqueous layer was acidified and the product obtained which was 2.4 g of substance, identified by suitable analytical techniques as being the subject compound.

The following is a table of certain selected compounds that are preparable according to the procedure described hereto. Compound numbers are assigned to each compound and are used throughout the remainder of the application.

Preferred compounds for use in the invention are those shown in Table I with the designations:

| Cmpd. No. | Chemical Name |
| --- | --- |
| 4 | 2-(2-m-trifluoromethylphenyl)-acetyl-1,3-cyclohexanedione |
| 5 | 2-(4-methylphenyl)-acetyl-1,3-cyclohexanedione |
| 8 | 2-(4-chlorophenyl)-acetyl-1,3-cyclohexanedione |
| 11 | 2-(2-p-trifluoromethylphenyl)-acetyl-1,3-cyclohexanedione |
| 12 | 2-(3,4-methylenedioxyphenylacetyl)-1,3-cyclohexanedione |
| 14 | 2-(2-p-fluorophenyl)-acetyl-1,3-cyclohexanedione |
| 24 | 2-(p-bromophenylacetyl)-1,3-cyclohexanedione |
| 26 | 2-[2-(1,4-benzodioxan-6-yl)-acetyl]-1,3-cyclohexanedione |
| 29 | 2-[2-(2-bromo-4,5-dimethoxyphenyl)-acetyl]-1,3-cyclohexanedione |
| 30 | 2-[2-(2-chloro-4,5-methylenedioxyphenyl)-acetyl]- |

-continued

| Cmpd. No. | Chemical Name |
|---|---|
| | 1,3-cyclohexanedione |

TABLE I

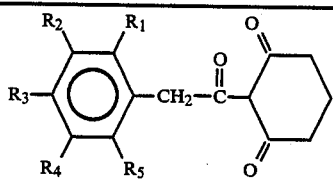

| Compound Number | $R_1$ | $R_2$ | $R_3$ | $R_4$ | $R_5$ | $N_D^{10}$ or m.p. °C. |
|---|---|---|---|---|---|---|
| 1 | Cl | H | H | H | H | 50-55 |
| 2 | Cl | H | H | H | Cl | 157-161 |
| 3 | Cl | H | Cl | H | H | 100-103 |
| 4 | H | $CF_3$ | H | H | H | semi-solid |
| 5 | H | H | $CH_3$ | H | H | 59-62 |
| 6 | $CH_3$ | H | H | H | H | 68-72 |
| 7 | H | $CH_3$ | H | H | H | 53-56 |
| 8 | H | H | Cl | H | H | 74-80 |
| 9 | H | $NO_2$ | H | H | H | 84-88 |
| 10 | $CF_3$ | H | H | H | H | 68-71 |
| 11 | H | H | $CF_3$ | H | H | 94-97 |
| 12 | H | —$OCH_2$—O— | | H | H | semi-solid |
| 13 | H | F | H | H | H | 54-61 |
| 14 | H | H | F | H | H | 82-86 |
| 15 | H | H | OMe | H | H | semi-solid |
| 16 | H | Cl | H | H | H | 78-83 |
| 17 | H | Cl | Cl | H | H | 70-73 |
| 18 | H | H | H | H | H | 58-66 |
| 19 | H | MeO | MeO | H | H | semi-solid |
| 20 | H | H | $NO_2$ | H | H | 119-125 |
| 21 | F | H | H | H | H | 72-75 |
| 22 | H | MeO | H | H | H | oil |
| 23 | MeO | H | H | MeO | H | 85-89 |
| 24 | H | H | Br | H | H | 105-109 |
| 25 | H | H | EtO | H | H | 70-73 |
| 26 | H | —$OCH_2CH_2O$— | | H | H | semi-solid |
| 27 | H | MeO | MeO | MeO | H | oil |
| 28 | H | Br | H | H | H | 81-85 |
| 29 | Br | H | MeO | H | H | 117-119 |
| 30 | H | —$OCH_2O$— | | H | Cl | 93-99 |
| 31 | H | Br | MeO | H | H | 87-89 |
| 32 | Br | H | H | H | H | 61-64 |
| 33 | Cl | Cl | H | H | Cl | semi-solid |
| 34 | H | H | MeS | H | H | oil |
| 35 | H | H | $MeSO_2$ | H | H | oil |
| 36 | H | —$OCH_2O$— | | H | Br | oil |

Herbicidal Screening Tests

As previously mentioned, the herein described compounds produced in the above-described manner are phytotoxic compounds which are useful and valuable in controlling various plant species. Selected compounds of this invention were initially screened as herbicides in the following manner.

Pre-emergence herbicide test. On the day preceding treatment, seeds of a number different weed species are planted in loamy sand soil in individual rows using one species per row across the width of a flat. The seeds used are green foxtail (FT) (*Setaria viridis*), watergrass (WG) (*Echinochloa crusgalli*), wild oat (WO) (*Avena fatua*), annual morningglory (AMG) (*Ipomoea lacunosa*), velvetleaf (VL) (*Abutilon theophrasti*), Indian mustard (MD) (*Brassica juncea*), curly dock (CD) (*Rumex crispus*), redroot pigweed (PW) (*Amaranthus retroflexus*), and yellow nutsedge (YNG) (*Cyperus esculentus*). Among seeds are planted to give about 20 to 40 seedlings per row, after emergence, depending upon the size of the plants.

Using an analytical balance, 333 milligrams (mg) of the compound to be tested are weighed into a 60 milliliter (ml) wide-mouth clear bottle and dissolved in 25 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 Kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each speices as percent control with 0% representing no injury and 100% representing complete control.

The results of the tests are shown in the following Table II.

TABLE II

Pre-Emergence Herbicidal Activity
Application Rate - 4.48 kg/ha

| Cmpd. No. | FT | WG | WO | AMG | VL | MD | CD | PW | YNS |
|---|---|---|---|---|---|---|---|---|---|
| 3 | 30 | 85 | 20 | 65 | 100 | 90 | — | 100 | 90 |
| 4 | 30 | 80 | 0 | 65 | 100 | 95 | — | 65 | 60 |
| 5 | 20 | 55 | 0 | 50 | 80 | 65 | — | 95 | 95 |
| 10 | 10 | 10 | 0 | 70 | 100 | 85 | — | 85 | 90 |
| 12 | 100 | 100 | 10 | 90 | 100 | 100 | — | 95 | 95 |
| 13 | 10 | 10 | 0 | 0 | 40 | 30 | — | 20 | 60 |
| 15 | 85 | 85 | 0 | 65 | 80 | 80 | — | 100 | 95 |
| 16 | 10 | 30 | 0 | 20 | 80 | 65 | — | 65 | 56 |
| 17 | 10 | 30 | 0 | 20 | 95 | 80 | — | 60 | 55 |
| 12 | 45 | 45 | 0 | 40 | 40 | 30 | — | 35 | 75 |
| 24 | 45 | 80 | 0 | 20 | 100 | 100 | — | 90 | 90 |
| 25 | 50 | 95 | 0 | 20 | 60 | 70 | — | 80 | 0 |
| 26 | 85 | 95 | 40 | 55 | 100 | 85 | — | 95 | 95 |
| 30 | 10 | 10 | 0 | 10 | 10 | 15 | 40 | — | 95 |
| 19 | 0 | 20 | 0 | 0 | 0 | 20 | 90 | — | 0 |
| 21 | 30 | 20 | 0 | 20 | 20 | 40 | 20 | — | 65 |
| 27 | 10 | 10 | 0 | 0 | 0 | 0 | 0 | — | 0 |
| 28 | 0 | 0 | 40 | 40 | 100 | 70 | 60 | — | 40 |
| 29 | 80 | 80 | 10 | 60 | 90 | 90 | 90 | — | 0 |
| 32 | 0 | 0 | 0 | 20 | 80 | 80 | 20 | — | 80 |
| 33 | 20 | 40 | 0 | 20 | 100 | 100 | 80 | — | 10 |
| 34 | 10 | 45 | 0 | 5 | 20 | 20 | 20 | — | 30 |
| 35 | 0 | 0 | 0 | 0 | 0 | 0 | 0 | — | 60 |
| 36 | 0 | 70 | 0 | 20 | 40 | 40 | 20 | — | 100 |

— Indicates not tested.

Post-Emergence Herbicide Test: This test is conducted in an identical manner to the testing procedure for the pre-emergence herbicide test, except the seeds of the different weed species are planted 10-12 days before treatment. Also, watering of the treated flats is confined to the soil surface and not to the foliage of the sprouted plants.

The results of the post-emergence herbicide test are reported in Table III.

TABLE III

Post-Emergence Herbicidal Activity
Application Rate - 4.48 kgha

| Cmpd. No. | FT | WG | WO | AMG | VL | MD | CD | PW | YNS |
|---|---|---|---|---|---|---|---|---|---|
| 3 | 20 | 40 | 45 | 65 | 75 | 55 | — | 20 | 45 |
| 4 | 85 | 90 | 55 | 100 | 100 | 100 | — | 100 | 65 |
| 9 | 0 | 0 | 0 | 65 | 85 | 0 | — | 20 | 35 |
| 5 | 10 | 10 | 20 | 55 | 100 | 35 | — | 80 | 80 |
| 8 | 45 | 60 | 0 | 75 | 100 | 85 | — | 95 | 85 |
| 10 | 45 | 35 | 20 | 75 | 100 | 95 | — | 90 | 55 |
| 11 | 65 | 85 | 10 | 85 | 100 | 100 | — | 65 | 75 |
| 12 | 100 | 100 | 45 | 85 | 100 | 100 | — | 100 | 95 |
| 13 | 45 | 35 | 10 | 40 | 90 | 90 | — | 80 | 30 |
| 14 | 85 | 65 | 20 | 70 | 100 | 100 | — | 100 | 85 |
| 15 | 90 | 85 | 80 | 75 | 100 | 100 | — | 100 | 90 |
| 16 | 90 | 20 | 20 | 80 | 100 | 95 | — | 75 | 65 |
| 17 | 20 | 20 | 10 | 65 | 95 | 85 | — | 85 | 20 |
| 12 | 45 | 35 | 25 | 65 | 100 | 95 | — | 65 | 65 |
| 22 | 45 | 20 | 10 | 35 | 85 | 20 | — | 50 | 50 |
| 24 | 30 | 10 | 0 | 10 | 80 | 40 | — | 40 | 55 |
| 25 | 45 | 55 | 80 | 10 | 85 | 75 | — | 55 | 20 |
| 26 | 65 | 85 | 85 | 60 | 60 | 75 | — | 55 | 85 |
| 30 | 0 | 10 | 0 | 5 | 0 | 0 | 0 | — | 30 |
| 19 | 30 | 40 | 20 | 20 | 20 | 40 | 70 | — | 10 |
| 21 | 40 | 40 | 0 | 45 | 85 | 55 | 95 | — | 65 |
| 27 | 60 | 75 | 75 | 20 | 60 | 50 | 50 | — | 25 |
| 28 | 0 | 0 | 0 | 20 | 100 | 0 | 20 | — | 0 |
| 29 | 10 | 20 | 0 | 10 | 10 | 10 | 40 | — | 0 |
| 32 | 20 | 10 | 0 | 0 | 0 | 0 | 0 | — | 0 |
| 33 | 40 | 20 | 0 | 30 | 20 | 20 | 80 | — | 0 |
| 34 | 100 | 60 | 60 | 20 | 60 | 50 | 20 | — | 60 |
| 35 | 100 | 60 | 60 | 40 | 40 | 40 | 80 | — | 50 |
| 36 | 60 | 40 | 40 | 10 | 30 | 20 | 60 | — | 60 |

— Indicates not tested.

Those compounds that passed the initial screening test were then further tested at varying rates against a wider variety of weeds, both grasses and broadleaf and crops and in pre-emergence and post-emergence tests.

EXAMPLE IV

Herbicidal Activity Tests

This example offers herbicidal activity test data to show the effectiveness of the cyclohexanediones at varying rates of application. The effect is observed by comparing the extent of weed control in test flats treated with the cyclohexanediones against that occurring in similar control flats. The soil used in these tests was a sandy loam soil from the Livermore, Calif. area.

Also added to the soil was 17-17-17 fertilizer (N-$P_2O_5$-$K_2O$ on a weight basis), amounting to 50 ppm by weight with respect to the soil, and Captan, a soil fungicide.

The treated soil was then placed in flats which were 3 inches deep, 6 inches wide, and 10 inches long. The soil was tamped and leveled with a row marker to impress six rows across the width of the flat. The test weeds were as follows:

| COMMON NAME | SCIENTIFIC NAME | ABBREVIATION |
|---|---|---|
| Broadleaf Weeds: | | |
| annual morningglory | *Ipomoea purpurea* | AMG |
| cocklebur | *Xanthium sp.* | CB |
| jimsonweed | *Datura stamonium* | JW |
| velvetleaf | *Abutilon theophrasti* | VL |
| mustard | *Brassica sp.* | MD |
| nighshade | *Solanum sp.* | SP |
| pigweed | *Amaranthus sp.* | PW |
| Grasses: | | |
| yellow nutsedge | *Cyperus exculentus* | YNS |
| downybrome | *Bromus tectorum* | DB |
| foxtail | *Setaria sp.* | FT |
| annual ryegrass | *Lolium multiflorum* | ARG |
| watergrass | *Echinochloa crusgalli* | WG |
| rox-orange sorghum | *Sorghum bicolor* | SHC |
| wild oat | *Avena fatua* | WO |
| broadleaf signalgrass | *Brachiaria platyphylla* | BSG |
| Crops: | | |
| wheat | (*Triticum aestivcum*) | WH |
| sugar beets | (*Beta vulgaris*) | SB |
| soybeans | (*Glycine max*) | SOY |
| corn | (*Zea mays*) | CN |
| milo | (*Sorghum bicolor*) | ML |
| cotton | (*Gossypium hirsutum*) | COT |
| rice | (*Oryza sativa*) | RC |

Sufficient seeds were planted to produce several seedlings per inch in each row. The flats were then placed in a greenhouse maintained at 70° to 85° F. (21° to 30° C.) and watered daily by sprinkler.

In the pre-emergent tests, chemical application was made just prior to planting, while in the post-emergent tests, chemical application is made by spraying 12 days after planting. The spray solution is prepared by dissolving 60 mg of herbicide compound in 20 ml of acetone containing 1% Tween® 20 (polyoxysorbitan monolaurate), then adding 20 ml of water to the resulting solution. The solution is sprayed at 80 gallon/acre, resulting in a 4 lb/acre rate of chemical application. Other rates were achieved by varying the solution concentration and/or the rate of spray.

Approximately 12-14 days after treatment, the degree of weed control was estimated and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in the Tables below. It is clear that the compounds of this invention are effective herbicides.

TABLE IV

HERBICIDE TEST RESULTS

| Compound Number | Application Rate (lb/A) | Method | Percent Control | | | | | | | | | | | | | | | |
|---|---|---|---|---|---|---|---|---|---|---|---|---|---|---|---|---|---|---|
| | | | PW | JW | PS | DB | FT | ARG | WG | SHC | WO | BSG | AMG | SES | VL | SP | MD | YNS | CB |
| 3 | 1.00 | PRE | 0 | 100 | — | 0 | 40 | 20 | 0 | 25 | 0 | — | 75 | 100 | 100 | −1 | 100 | 80 | 35 |
| | 2.00 | PRE | 40 | 100 | 20 | 0 | 0 | 65 | 40 | 20 | 35 | — | 85 | 100 | 100 | −1 | 100 | 95 | 60 |
| 4 | 0.25 | POST | 0 | — | 20 | 0 | 0 | 0 | 0 | 0 | 0 | — | 20 | 20 | 20 | — | 40 | 0 | 0 |
| | 0.50 | POST | 20 | — | 30 | 0 | 0 | 0 | 0 | 10 | 0 | — | 30 | 50 | 30 | — | 45 | 30 | 20 |
| | 1.00 | POST | 25 | — | 40 | 0 | 10 | 0 | 30 | 20 | 10 | — | 45 | 55 | 40 | — | 55 | 35 | 30 |
| | 2.00 | POST | 30 | — | 55 | 0 | 30 | 0 | 45 | 60 | 15 | — | 60 | 75 | 90 | — | 60 | 80 | 35 |

TABLE IV-continued
HERBICIDE TEST RESULTS

| Compound Number | Application Rate (lb/A) | Method | PW JW | PS | DB | FT | ARG | WG | SHC | WO | BSG | AMG | SES VL | SP | MD | YNS | CB |
|---|---|---|---|---|---|---|---|---|---|---|---|---|---|---|---|---|---|
| 4 | 1.00 | PRE | 25 — | — | 0 | 0 | 0 | 0 | — | 0 | — | 35 | 20 −1 | 0 | −1 | 40 | 0 |
|   | 2.00 | PRE | 35 — | — | 0 | 0 | 0 | 30 | — | 0 | — | 70 | 50 −1 | 30 | −1 | 55 | 30 |
| 5 | 1.00 | POST | 0 — | — | 0 | 0 | 0 | 0 | 10 | 0 | — | 10 | 0 40 | — | 20 | 30 | 0 |
|   | 2.00 | POST | 30 — | — | 0 | 0 | 0 | 20 | 35 | 0 | — | 30 | 20 60 | — | 35 | 45 | 0 |
|   | 1.00 | PRE | 0 — | — | 0 | 0 | 0 | 10 | 0 | 0 | — | 20 | 20 50 | 0 | 0 | 45 | 50 |
|   | 2.00 | PRE | 0 — | — | 0 | 20 | 0 | 60 | 0 | 0 | — | 30 | 20 100 | 20 | 30 | 85 | 65 |
| 8 | 1.00 | POST | 20 — | — | 0 | 0 | 0 | 0 | 25 | 0 | — | 20 | 0 35 | — | 20 | 30 | 0 |
|   | 2.00 | POST | 40 — | — | 0 | 0 | 0 | 35 | 35 | 0 | — | 35 | 15 50 | — | 45 | 45 | 10 |
| 8 | 0.25 | PRE | 0 — | — | 0 | 0 | 0 | 0 | 0 | 0 | — | 10 | 20 100 | 0 | 35 | 40 | 0 |
|   | 0.50 | PRE | 0 — | — | 0 | 0 | 0 | 0 | 0 | 0 | — | 20 | 35 100 | 0 | 80 | 50 | 20 |
|   | 1.00 | PRE | — — | — | — | — | — | — | — | — | — | 50 | — — | — | — | — | 30 |
| 8 | 1.00 | PRE | 30 — | — | 20 | 0 | — | 35 | 0 | 0 | — | — | 60 100 | 40 | 100 | 80 | 40 |
|   | 2.00 | PRE | 65 — | — | 35 | 35 | 35 | 80 | 20 | 0 | — | 70 | 75 100 | 65 | 100 | — | 70 |
| 8 | 1.00 | POST | 0 — | — | 0 | 20 |   | 40 | 20 | 0 | — | — | 75 100 | 35 | 50 | 40 |   |
|   | 2.00 | POST | 30 |   | 25 | 80 | 30 | 80 | 40 | 0 | — | 80 | 100 100 | 50 | 100 | 95 | 100 |
| 9 | 1.00 | PRE | 0 — | — | 0 | 0 | 0 | 0 | 0 | 0 | — | 30 | 20 75 | 0 | 50 | 25 | 20 |
|   | 2.00 | PRE | 0 — | — | 0 | 0 | 0 | 30 | 40 | 0 | — | 45 | 50 100 | 20 | 55 | 55 | 35 |
| 10 | 1.00 | POST | 35 — | — | 0 | 20 | 0 | 45 | 30 | 0 | — | 35 | 40 30 | 30 | 20 | 35 | 20 |
|   | 2.00 | POST | 50 — | — | 10 | 40 | 0 | 55 | 45 | 20 | — | 45 | 55 45 | 40 | 45 | 45 | 30 |
| 10 | 0.25 | PRE | 0 — | — | 0 | 10 | 0 | 10 | 0 | 0 | — | 0 | 40 0 | 0 | 40 | 0 | 0 |
|   | 0.50 | PRE | 0 — | — | 0 | 10 | 0 | 10 | 0 | 0 | — | 0 | 55 100 | 0 | 50 | 10 | 0 |
|   | 1.00 | PRE | 0 — | — | 0 | 20 | 35 | 30 | 0 | 0 | — | 50 | 65 100 | 20 | 55 | 30 | 0 |
|   | 2.00 | PRE | 0 — | — | 20 | 30 | 45 | 35 | 0 | 0 | — | 65 | 95 100 | 30 | 65 | 75 | 50 |
| 11 | 1.00 | POST | 38 — | — | 10 | 30 | 0 | 60 | 30 | 0 | — | 35 | 45 35 | 40 | 20 | 50 | 35 |
|   | 2.00 | POST | 55 — | — | 30 | 60 | 0 | 75 | 45 | 0 | — | 45 | 60 70 | 35 | 55 | 75 | 55 |
| 11 | 0.25 | PRE | 0 — | — | 0 | 0 | 0 | 45 | 20 | 0 | — | 30 | 0 70 | 0 | 40 | 35 | 0 |
|   | 0.50 | PRE | 30 — | — | 0 | 30 | 0 | 70 | 30 | 0 | — | 40 | 30 100 | 20 | 197 | 45 | 0 |
|   | 1.00 | PRE | 40 — | — | 0 | 40 | 0 | 80 | 55 | 0 | — | 65 | 50 100 | 35 | 70 | 75 | 35 |
|   | 2.00 | PRE | 50 — | — | 0 | 50 | 20 | 95 | 70 | 0 | — | 80 | 55 100 | 45 | 95 | 85 | 80 |
| 12 | 0.25 | POST | 30 — | — | 0 | 20 | 20 | 80 | 0 | 0 | — | 30 | 40 40 | 0 | 20 | 20 | 35 |
|   | 0.50 | POST | 40 — | — | 20 | 45 | 30 | 85 | 20 | 0 | — | 40 | 65 50 | 20 | 35 | 30 | 45 |
|   | 1.00 | POST | 56 — | — | 70 | 35 | 90 | 35 | 20 | 0 | — | 50 | 80 60 | 40 | 60 | 50 | 30 |
|   | 2.00 | POST | 70 — | — | 45 | 80 | 48 | 95 | 45 | 0 | — | 55 | 90 70 | 55 | 70 | 65 | 70 |
| 13 | 1.00 | POST | 20 — | — | 10 | 35 | 0 | 35 | 30 | 0 | — | 30 | 60 45 | 20 | 30 | 20 | 35 |
|   | 2.00 | POST | 40 — | — | 20 | 50 | 0 | 50 | 45 | 35 | — | 40 | 75 70 | 40 | 50 | 30 | 45 |
| 14 | 0.25 | POST | 0 — | — | 0 | 0 | 0 | 20 | 10 | 0 | — | 0 | 20 40 | 0 | 10 | 40 | 0 |
|   | 0.50 | POST | 10 — | — | 0 | 10 | 0 | 30 | 20 | 0 | — | 0 | 35 50 | 20 | 20 | 50 | 0 |
|   | 1.00 | POST | 20 — | — | 0 | 20 | 30 | 55 | 35 | 0 | — | 20 | 40 60 | 30 | 40 | 60 | 20 |
|   | 2.00 | POST | 40 — | — | 35 | 55 | 45 | 75 | 50 | 30 | — | 40 | 60 75 | 40 | 50 | 85 | 30 |
| 14 | 0.25 | PRE | 0 — | — | 0 | 20 | 35 | 50 | 20 | 0 | — | 10 | 40 50 | 0 | 20 | 40 | 0 |
|   | 0.50 | PRE | 0 — | — | 30 | 30 | 45 | 70 | 30 | 0 | — | 20 | 50 60 | 0 | 40 | 50 | 20 |
|   | 1.00 | PRE | 0 — | — | 40 | 40 | 65 | 80 | 40 | 0 | — | 45 | 70 100 | 30 | 80 | 80 | 35 |
|   | 2.00 | PRE | 40 — | — | 75 | 65 | 75 | 90 | 65 | 0 | — | 65 | 100 100 | 45 | 90 | 90 | 55 |
| 15 | 0.25 | POST | 0 — | — | 0 | 35 | 0 | 55 | 10 | 0 | — | 0 | 10 20 | 0 | 10 | 40 | 0 |
|   | 0.50 | POST | 20 — | — | 0 | 45 | 20 | 70 | 20 | 0 | — | 0 | 30 30 | 0 | 30 | 50 | 0 |
|   | 1.00 | POST | 30 — | — | 20 | 55 | 30 | 75 | 30 | 20 | — | 20 | 60 70 | 0 | 40 | 75 | 30 |
|   | 2.00 | POST | 35 — | — | 35 | 70 | 40 | 90 | 50 | 50 | — | 35 | 75 75 | 40 | 55 | 90 | 40 |
| 15 | 0.25 | PRE | 0 — | — | 0 | 20 | 0 | 50 | 0 | 0 | — | 0 | 40 40 | 0 | 0 | 30 | 0 |
|   | 0.50 | PRE | 0 — | — | 0 | 30 | 0 | 65 | 0 | 0 | — | 0 | 50 50 | 0 | 0 | 40 | 0 |
|   | 1.00 | PRE | 30 — | — | 0 | 55 | 0 | 90 | 25 | 0 | — | 20 | 60 60 | 0 | 30 | 80 | 40 |
|   | 2.00 | PRE | 45 — | — | 0 | 80 | 0 | 95 | 35 | 0 | — | 40 | 75 100 | 0 | 50 | 95 | 60 |
| 12 | 1.00 | POST | 20 — | — | 0 | 20 | 20 | 20 | 25 | 0 | — | 20 | 40 35 | 35 | 30 | 20 | 35 |
|   | 2.00 | POST | 45 — | — | 0 | 45 | 30 | 40 | 40 | 0 | — | 45 | 55 50 | 50 | 45 | 40 | 50 |
| 22 | 1.00 | PRE | 0 — | — | 0 | 20 | 0 | 30 | 0 | 0 | — | 0 | 20 70 | 0 | 20 | 0 | 20 |
|   | 2.00 | PRE | 0 — | — | 20 | 40 | 30 | 45 | 0 | 0 | — | 45 | 55 100 | 0 | 55 | 65 | 35 |
| 24 | 0.25 | PRE | 0 — | — | 0 | 0 | 0 | 0 | 0 | 0 | — | 0 | 0 60 | 0 | 50 | 0 | 0 |
|   | 0.50 | PRE | 0 — | — | 0 | 20 | 10 | 0 | 0 | 0 | — | 0 | 0 100 | 0 | 70 | 20 | 0 |
|   | 1.00 | PRE | 20 — | — | 0 | 30 | 20 | 40 | 0 | 0 | — | 20 | 35 100 | 30 | 80 | 60 | 20 |
|   | 2.00 | PRE | 30 — | — | 0 | 40 | 35 | 70 | 0 | 0 | — | 30 | 75 100 | 45 | 90 | 90 | 35 |
| 25 | 0.25 | POST | 0 — | — | 0 | 20 | 0 | 30 | 0 | 0 | — | 20 | 0 0 | 0 | 0 | 20 | 0 |
|   | 0.50 | POST | 20 — | — | 0 | 35 | 0 | 40 | 0 | 0 | — | 30 | 20 20 | 0 | 30 | 30 | 0 |
|   | 1.00 | POST | 30 — | — | 0 | 55 | 0 | 75 | 20 | 30 | — | 40 | 30 40 | 30 | 50 | 35 | 20 |
|   | 2.00 | POST | 40 — | — | 20 | 70 | 40 | 85 | 30 | 45 | — | 45 | 45 50 | 40 | 60 | 40 | 45 |
| 25 | 1.00 | PRE | 0 — | — | 10 | 30 | 10 | 70 | 20 | 0 | — | 0 | 35 40 | 0 | 50 | 0 | 0 |
|   | 2.00 | PRE | 0 — | — | 30 | 50 | 35 | 80 | 35 | 20 | — | 0 | 50 65 | 0 | 100 | 0 | 0 |
| 29 | 2.00 | PRE | — — | — | 0 | 90 | 0 | 99 | 30 | 0 | 80 | 25 | 100 100 | 50 | 100 | 0 | 60 |
|   | 1.00 | PRE | — — | — | 0 | 60 | 0 | 95 | 20 | 0 | 70 | 25 | 60 100 | 40 | 100 | 0 | 25 |
|   | 0.50 | PRE | — — | — | 0 | 15 | 0 | 20 | 10 | 0 | 40 | 20 | 45 100 | 30 | 85 | 0 | 15 |
| 30 | 2.00 | POST | — — | — | 10 | 0 | 10 | 95 | 0 | 0 | 97 | 100 | 100 100 | 30 | 90 | 85 | 70 |
|   | 0.50 | POST | — — | — | 10 | 0 | 5 | 40 | 0 | 0 | 65 | 30 | 100 100 | 0 | 65 | 85 | N |

TABLE V
HERBICIDE TEST RESULTS

| Compound Number | Application Rate (lb/A) | Method | Crops SOY | WH | ML | RC | SB | CN | COT |
|---|---|---|---|---|---|---|---|---|---|
| 3 | 1.00 | PRE | 25 | 0 | 0 | 0 | 100 | 0 | 25 |
|   | 2.00 | PRE | 40 | 0 | 0 | 35 | 100 | 25 | 35 |
| 4 | 0.25 | POST | 20 | 0 | 0 | 0 | 0 | 10 | 0 |
|   | 0.50 | POST | 35 | 0 | 0 | 0 | 40 | 15 | 30 |
|   | 1.00 | POST | 50 | 0 | 10 | 20 | 45 | 20 | 45 |
|   | 2.00 | POST | 60 | 20 | 15 | 30 | 65 | 40 | 55 |
| 4 | 1.00 | PRE | 0 | 0 | 0 | 0 | 50 | 10 | 20 |
|   | 2.00 | PRE | 20 | 0 | 0 | 20 | 90 | 20 | 40 |
| 5 | 1.00 | POST | 40 | 0 | 20 | 10 | 50 | 0 | 10 |
|   | 2.00 | POST | 50 | 0 | 30 | 20 | 60 | 20 | 35 |
|   | 1.00 | PRE | 0 | 0 | 0 | 0 | 60 | 0 | 0 |
|   | 2.00 | PRE | 0 | 0 | 0 | 40 | 90 | 0 | 30 |
| 8 | 1.00 | POST | 40 | 0 | 20 | 0 | 50 | 0 | 35 |
|   | 2.00 | POST | 50 | 0 | 30 | 20 | 60 | 30 | 50 |
| 8 | 0.25 | PRE | 0 | 0 | 0 | 0 | 40 | 0 | 0 |
|   | 0.50 | PRE | 0 | 0 | 0 | 0 | 80 | 0 | 0 |
|   | 1.00 | PRE | — | — | — | — | — | — | — |
| 8 | 1.00 | PRE | 0 | 0 | 0 | 0 | 90 | 0 | 35 |
|   | 2.00 | PRE | 0 | 0 | 0 | 35 | 100 |   | 65 |
| 8 | 1.00 | POST | 0 | 0 | 0 | 20 | 90 | 0 | 50 |
|   | 2.00 | POST | 0 | 0 | 0 | 45 | 100 | 0 | 60 |
| 9 | 1.00 | PRE | 0 | 0 | 15 | 0 | 60 | 0 | 20 |
|   | 2.00 | PRE | 20 | 0 | 35 | 0 | 90 | 20 | 35 |
| 10 | 0.25 | PRE | 0 | 0 | 0 | 0 | 40 | 0 | 0 |
|    | 0.50 | PRE | 0 | 0 | 0 | 0 | 60 | 0 | 25 |
|    | 1.00 | PRE | 35 | 0 | 0 | 0 | 100 | 0 | 60 |
|    | 2.00 | PRE | 45 | 0 | 35 | 20 | 50 | 20 | 55 |
|    |      |     | 65 | 20 | 40 | 30 | 60 | 40 | 60 |
| 11 | 1.00 | POST | 40 | 0 | 20 | 0 | 50 | 20 | 40 |
|    | 2.00 | POST | 60 | 20 | 40 | 20 | 60 | 35 | 60 |
| 11 | 0.25 | PRE | 0 | 0 | 0 | 20 | 40 | 0 | 0 |
|    | 0.50 | PRE | 0 | 0 | 20 | 30 | 70 | 0 | 20 |
|    | 1.00 | PRE | 0 | 0 | 40 | 50 | 80 | 0 | 50 |
|    | 2.00 | PRE | 0 | 0 | 50 | 65 | 100 | 0 | 80 |
| 12 | 0.25 | POST | 40 | 0 | 0 | 0 | 40 | 0 | 40 |
|    | 0.50 | POST | 50 | 0 | 10 | 0 | 60 | 0 | 45 |
|    | 1.00 | POST | 55 | 0 | 20 | 10 | 70 | 30 | 50 |
|    | 2.00 | POST | 80 | 30 | 35 | 40 | 85 | 55 | 60 |
| 13 | 1.00 | POST | 30 | 0 | 35 | — | 40 | 20 | — |
|    | 2.00 | POST | 50 | 0 | 45 | — | 60 | 30 | 0 |
| 14 | 0.25 | POST | 10 | 0 | 40 | — | 35 | 0 | — |
|    | 0.50 | POST | 20 | 0 | 50 | — | 45 | 0 | — |
|    | 1.00 | POST | 40 | 0 | 60 | — | 50 | 20 | — |
|    | 2.00 | POST | 50 | 20 | 85 | — | 60 | 30 | — |
| 14 | 0.25 | PRE | — | 0 | — | — | 20 | — | — |
|    | 0.50 | PRE | 20 | 0 | 40 | — | 100 | 0 | — |
|    | 1.00 | PRE | 40 | 0 | 50 | — | 100 | 20 | — |
|    | 2.00 | PRE | 80 | 0 | 80 | — | 100 | 35 | — |
| 15 | 0.25 | POST |   | 0 | — | — | 40 | — | — |
|    | 0.50 | POST | 10 | 0 | 40 | — | 60 | 0 | — |
|    | 1.00 | POST | 30 | 0 | 50 | — | 70 | 0 | — |
|    | 2.00 | POST | 40 | 0 | 75 | — | 75 | 30 | — |
| 15 | 0.25 | PRE | 55 | 0 | 90 | — | 80 | 40 | — |
|    | 0.50 | PRE | — | 0 | — | — | 90 | — | — |
|    | 1.00 | PRE | 0 | 0 | 30 | — | 100 | 0 | — |
|    | 2.00 | PRE | 0 | 0 | 40 | — | 100 | 0 | — |
| 12 | 1.00 | POST | 45 | 0 | 0 | 0 | 35 | 0 | 35 |
|    | 2.00 | POST | 60 | 0 | 20 | 30 | 55 | 30 | 55 |
| 22 | 1.00 | PRE | 0 | 0 | 0 | 20 | 90 | 0 | 35 |
|    | 2.00 | PRE | 30 | 0 | 0 | 25 | 100 | 0 | 40 |
| 24 | 0.25 | PRE | 0 | 0 | 0 | 0 | 45 | 0 | 0 |
|    | 0.50 | PRE | 0 | 0 | 0 | 0 | 80 | 0 | 20 |
|    | 1.00 | PRE | 0 | 0 | 0 | 20 | 100 | 0 | 45 |
|    | 2.00 | PRE | 0 | 0 | 0 | 30 | 100 | 0 | 50 |
| 25 | 0.25 | POST | 0 | 0 | 0 | 0 | 0 | 0 | 40 |
|    | 0.50 | POST | 0 | 0 | 0 | 0 | 30 | 0 | 45 |
|    | 1.00 | POST | 20 | 0 | 20 | 30 | 40 | 30 | 50 |
|    | 2.00 | POST | 50 | 0 | 30 | 40 | 50 | 35 | 55 |
| 25 | 1.00 | PRE | 0 | 0 | 0 | 0 | 60 | 0 | 20 |
|    | 2.00 | PRE | 0 | 0 | 0 | 35 | 90 | 10 | 35 |
| 29 | 2.00 | PRE | 0 | 0 | 70 | 65 | 100 | 20 | 45 |
|    | 1.00 | PRE | 0 | 0 | 50 | 60 | 100 | 20 | 45 |
|    | 0.50 | PRE | 0 | 0 | 40 | 25 | 100 | 20 | 25 |

— indicates not tested

The compounds of the present invention are useful as herbicides, especially as pre-emergence herbicides, and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such heavy aromatic naphthas, kerosene or other petroleum fractions, or vegetable oils; and/or stickers such as destrins, glue or synthetic resins.

Typical wetting, dispersing or emulsifying agents used in agricultural formulations include, for example, the alkyl and alkylaryl sulfonates and sulfates and their sodium salts; polyhydric alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvant or in combination with any of the abovedescribed adjuvants. Other phytotoxic compounds useful in combination with the abovedescribed compounds include, for example, 2,4-dichlorophenoxyacetic acids, 2,4,5-trichlorophenoxyacetic acid, 2-methyl-4-chlorophenoxyacetic acid and the salts, esters and amides thereof, triazine derivatives, such as 2,4-bis-(3-methoxypropylamino)-6-methylthio-s-triazine, 2-chloro-4-ethylamino-6-isopropylamino-s-triazine, and 2-ethylamino-4-isopropyl amino-6-methylmercapto-s-triazine; urea derivatives, such as 3-(3,5-dichlorophenyl)-1,1-dimethylurea and 3-(p-chlorophenyl)-1,1-dimethylurea; and acetamides such as N,N-diallyl-α-chloroacetamide, and the like; benzoic acids such as 3-amino-2,5-dichlorogbenaoic acid; thiocarbamates such as S-propyl N,N-dipropylthiocarbamate, S-ethyl N,N-dipropylthiocarbamate, S-ethyl cyclohexylethyl thiocarbamate, S-ethyl hexahydro-1H-azepine-1-carbothioate and the like; anilines such as 4-(methylsulfonyL)-2,6-dinitro-N,N-substituted aniline, 4-trifluoromethyl-2,6-dinitro-N,N-di-n-propyl aniline and 4-trifluoromethyl-2,6-dinitro-N-ethyl-N,N-di-n-butyl aniline. Fertilizers useful in combination with the active ingredients include, for example, ammonium nitrate, urea and superphosphate. Other useful additaments include materials in which plant organisms take root and grow such as compost, manure, humus, sand, and the like.

We claim:

1. A compound having the structural formula

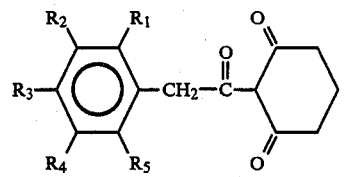

wherein $R_1$, $R_2$, $R_3$, $R_4$ and $R_5$ are the same or different and are selected from the group consisting of hydrogen, chlorine, bromine, iodine, nitro, trifluoromethyl, trifluoromethoxy, cyano, lower alkylsulfonyl, and alkylthio having from 1 to 4 carbon atoms, with the proviso that $R_1$, $R_2$, $R_3$ and $R_4$ are not all hydrogen.

2. The compound of claim 1 wherein $R_1$, $R_2$, $R_4$ and $R_5$ are hydrogen and $R_3$ is bromine.

3. The compound of claim 1 wherein $R_1$, $R_2$, $R_4$ and $R_5$ are hydrogen and $R_3$ is trifluoromethyl.

4. The compound of claim 1 wherein $R_1$, $R_2$, $R_4$ and $R_5$ are hydrogen and $R_3$ is chlorine.

* * * * *